(12) United States Patent
Bar-Or

(10) Patent No.: US 6,974,839 B2
(45) Date of Patent: Dec. 13, 2005

(54) METHOD OF DELAYING EJACULATION

(75) Inventor: David Bar-Or, Englewood, CO (US)

(73) Assignee: DMI BioSciences, Inc., Englewood, CO (US)

( * ) Notice: Subject to any disclaimer, the term of this patent is extended or adjusted under 35 U.S.C. 154(b) by 0 days.

(21) Appl. No.: 10/098,826

(22) Filed: Mar. 15, 2002

(65) Prior Publication Data

US 2002/0132857 A1 Sep. 19, 2002

Related U.S. Application Data

(60) Provisional application No. 60/276,806, filed on Mar. 16, 2001.

(51) Int. Cl.$^7$ .......................... A61K 31/135
(52) U.S. Cl. .................... 514/647
(58) Field of Search .................. 514/647

(56) References Cited

U.S. PATENT DOCUMENTS

| | | | |
|---|---|---|---|
| 3,652,589 A | 3/1972 | Flick et al. | 260/326.5 |
| 3,830,934 A | 8/1974 | Flick et al. | 424/330 |
| 4,507,323 A | 3/1985 | Stern | 514/649 |
| 4,940,731 A | 7/1990 | Bick | 514/657 |
| 5,151,448 A | 9/1992 | Crenshaw et al. | 514/651 |
| 5,223,541 A | 6/1993 | Maryanoff et al. | 514/644 |
| 5,276,042 A | 1/1994 | Crenshaw et al. | 514/321 |
| 5,336,691 A | 8/1994 | Raffa et al. | 514/629 |
| 5,468,744 A | 11/1995 | Raffa et al. | 514/282 |
| 5,516,803 A | 5/1996 | Raffa | 514/570 |
| 5,591,452 A | 1/1997 | Miller et al. | 424/468 |
| 5,601,842 A | 2/1997 | Bartholomaeus | 424/464 |
| 5,723,668 A | 3/1998 | Buschmann et al. | 564/304 |
| 5,728,885 A | 3/1998 | Buschmann et al. | 564/304 |
| 5,801,201 A | 9/1998 | Graudums et al. | 514/646 |
| 5,811,582 A | 9/1998 | Buschmann et al. | 564/355 |
| 5,874,620 A | 2/1999 | Lerman et al. | 564/443 |
| 5,919,826 A | 7/1999 | Caruso | 514/629 |
| 5,922,341 A | 7/1999 | Smith et al. | 424/430 |
| 5,929,122 A | 7/1999 | Reimann | 514/646 |
| 6,017,963 A | 1/2000 | Alfonso et al. | 514/646 |
| 6,037,360 A | 3/2000 | Smith et al. | 514/397 |
| 6,090,856 A | 7/2000 | Sasaki | 514/646 |
| 6,156,342 A | 12/2000 | Sriwongjanya et al. | 424/473 |
| 6,228,864 B1 | 5/2001 | Smith et al. | 514/288 |
| 6,297,286 B1 | 10/2001 | Huckle | 514/646 |
| 6,339,105 B1 | 1/2002 | Kamin et al. | 514/646 |
| 6,369,051 B1 | 4/2002 | Jenkins | 514/217.08 |
| 6,376,554 B1 | 4/2002 | Cheetham et al. | 514/646 |
| 6,399,618 B1 | 6/2002 | Zolotoy et al. | 514/255.01 |
| 6,403,597 B1 | 6/2002 | Wilson et al. | 514/256 |
| 2001/0049391 A1 | 12/2001 | Alfonso et al. | 514/564 |
| 2002/0052341 A1 | 5/2002 | Fang et al. | 514/58 |
| 2002/0055544 A1 | 5/2002 | Kamin et al. | 514/650 |

FOREIGN PATENT DOCUMENTS

GB     2 340 037     2/2000

(Continued)

OTHER PUBLICATIONS

Wilder-Smith et al., Br. J. Clin. Pharmacol., 1997;43:71-75.*

(Continued)

*Primary Examiner*—San-Ming Hui
(74) *Attorney, Agent, or Firm*—Sheridan Ross P.C.

(57) ABSTRACT

The invention provides a method of delaying ejaculation. The method comprises administering an effective amount of a tramadol material to a human male prior to sexual intercourse. The method is particularly useful for treating premature ejaculation.

17 Claims, 1 Drawing Sheet

(+) (R,R) cis (-) (S,S) cis (S,R) trans (R,S) trans

FOREIGN PATENT DOCUMENTS

| WO | WO 95/13072 | 11/1994 |
|----|-------------|---------|
| WO | WO 99/21508 | 5/1999 |
| WO | WO 00/67729 | 11/2000 |
| WO | WO 01/17521 | 3/2001 |
| WO | WO 01/59084 | 8/2001 |
| WO | WO 02/41883 | 5/2002 |

OTHER PUBLICATIONS

Jeffrey et al., British Journal of Anaesthesia, 1999; 83: 245-249.*

Gobbi et al., European Journal of Pharmacology, 1999; 370:23-26.*

Agmo et al., "Opioids and sexual behavior in the male rabbit: the role of central and peripheral opioid receptors". J Neural Transm Gen Sect 1994; 97(e):211-23. (abstract) [Retrieved Apr. 15, 2003]. Retrieved from PubMed, PMID: 7873130.

Balfour et al., "Activation of Ventral Tegmental Neurons Following Sexual Behavior in Male Rats", Horm. Behav., 39(4): 324 (2001).

Dunbar et al., "Concurrent Spinal Infusion of MK801 Blocks Spinal Tolerance and Dependence Induced by Chronic Intrathecal Morphine in the Rat", Anesthesiology, V. 84, No. 5, 1996, pp 1177-1188.

Frink et al., "Influence of Tramadol on Neurotransmitter Systems of the Rat Brain", Arzneim.-Forsch/Drug Res. 46 (II), Nr. 11 (1996), pp 1029-1036.

Gomez-Marrero et al., "Stimulation of opioid receptors suppresses penile erectile reflexes and seminal emission in rats". In: Pharmacol Biochem Behav, Oct. 1988:31(2): 393-6 (abstract) [Retrieved Apr. 15, 2003]. Retrieved from PubMed, PMID 2854263.

Jaw et al., "Involvement of kappa-opioid receptors in opioid dependence/withdrawal: studies using butorphanol". Eur J. Pharmacol, May 12, 1994, 247 (1-2): 153-60 (abstract) [Retrieved Apr. 15, 2003]. Retrieved from PubMed, PMID: 8082697.

Jaw et al., "Involvement of delta-opioid receptors in physical dependence on butorphanol". Eur J Pharmacol, Aug. 10, 1993, 240 (1): 67-72 (abstract) [Retrieved Apr. 15, 2003]. Retrieved from PubMed, PMID: 8405123.

Jaw et al., "Opioid antagonists and butorphanol dependence". Pharmacol Biochem Behav, Mar. 1993: 44(3) 497-500 (abstract) [Retrieved Jun. 16, 2002] Retrieved from PubMed, PMID: 8383850.

Leyton et al., "The stimulation of central kappa opioid receptors decreases male sexual behavior and locomotor activity". Brain Res Oct. 23, 1992, 594(1): 56-74. (abstract) [Retrieved Apr. 15, 2003] Retrieved from PubMed, PMID: 1334765.

Matuszewich, "Bilateral injections of a selective mu-receptor agonist (morphiceptin) into the medial preoptic nucleus produces a marked delay in the initiation of sexual behavior in the male rat". Psychopharmacology (Berl), 1992; 106(3): 391-6. (abstract) [Retrieved Apr. 15, 2003] Retrieved from PubMed, PMID: 1315063.

Melis et al. "Morphine injected into the paraventricular nucleus of the hypothalamus prevents noncontact penile erections and impairs copulation: involvement of nitric oxide." Eur J Neurosci, Jun. 1999, 11(6): 1857-64. (abstract) [Retrieved Apr. 15, 2003] Retrieved from PubMed, PMID: 10336653.

Paredes et al., "What do female rats like about sex? Paced mating." Behav Brain Res, Nov. 1, 1999; 105(1): 117-27. (abstract) [Retrieved May 1, 2003] Retrieved from PubMed, PMID: 10553695.

Rodriguez-Manzo et al., "Opioid antagonists and the sexual satiation phenomenon". Psychopharmacology (Berl), Nov. 1995, 122(2): 131-6. (abstract) [Retrieved May 1, 2003] Retrieved from PubMed, PMID: 8848528.

Sanchez et al., "Comparison of the Effects of Antidepressants and Their Metabolites on Reuptake of Biogenic Amines and on Receptor Binding", Cellular and Molecular Neurobiology, vol. 19, No. 4, 1999, pp 467-489.

Stahl, "Not So Selective Serotonin Reuptake Inhibitors", Jul. 1998, [Retrieved Apr. 2, 2003 from http://www.psychiatrist.com/pcc/brainstorm/br5907.htm].

Trynke et al., "Citalopram alone does not, but combined with a silent 5-$HT_{1A}$ receptor antagonist does inhibit male sexual behavior" [Retrieved Apr. 7, 2003 from http://www-nin.sci.kun.nl/NIN%20abstracts.htm].

Waldinger et al., "SSRIs and ejaculation: a double-blind, randomized, fixed-dose study with paroxetine and citalopram". J Clin Psychopharmacol, Dec. 2001, 21(6): 556-60. (absract) [Retrieved Mar. 31, 2003] Retrieved from PubMed, PMID: 11763001.

Waldinger et al., "Antidepressants and ejaculation: a double-blind, randomized, placebo-controlled, fixed-dose study with paroxetine, sertraline, and nefazodone". J Clin Psychopharmacol, Jun. 2001, 21(3): 293-7. (abstract) [Retrieved Mar. 31, 2003] Retrieved from PubMed, PMID: 11386492.

Waldinger et al., "Effect of SSRI antidepressants on ejaculation: a double-blind, randomized, placebo-controlled study with fluoxetine, fluvoxamine, paroxetine, and sertraline". J Clin Psychopharmacol, Aug. 1998, 18(4): 274-81. (abstract) [Retrieved Mar. 31, 2003] Retrieved from PubMed, PMID: 9690692.

Olivier et al., "Serotonin, serotonergic receptors, selective serotonin reuptake inhibitors and sexual behaviour". Int Clin Psychopharmacol, Jul. 1998, 13 Suppl 6:S9-14, (abstract) [Retrieved Mar. 31, 2003] Retrieved from PubMed, PMID: 9728669.

Waldinger, "Selective serotonin reuptake inhibitor-induced sexual dysfunction clinical and research considerations". Int Clin Psychopharmacol, Jul. 1998, 13 Suppl 6:S27-33. (abstract) [Retrieved Mar. 31, 2003] Retrieved from PubMed, PMID: 9728672.

Waldinger et al., "The selective serotonic re-uptake inhibitors fluvoxamine and paroxetine differ in sexual inhibitory effects after chronic treatment". Psychopharmacology (Berl), Mar. 2002, 160(3):283-9. (abstract) [Retrieved Apr. 7, 2003] Retrieved from PubMed, PMID: 11889497.

Balfour et al., "MU Opioid Receptor Activation in Ventral Tegmental Neurons Following Sexual Behavior", International Narcotics Research Conference, Monterey, CA, 2002.

Zarrindast et al., "Morphine inhibits dopaminergic and cholinergic induced ejaculation in rats". In: Gen Pharmacol, Jul. 1994, 25(4):803-8. (abstract) [Retrieved May 1, 2003] Retrieved from PubMed, PMID: 7958745.

"Link Found Between Pain, Immune, and Reproductive Systems", Indiana University School of Medicine, Apr. 21, 1997. [Retrieved Apr. 15, 2003 from http://medicine/indiana.edu/news_releases/archieve_97/pain2.htm].

"Opiates & Sexual Function", IDMU Ltd. 1994-2002. [Retrieved Apr. 15, 2003 from http://www.idmu.co.uk/opiatesex.htm].

Pybus et al.; "Opiates and Sexual Function"; *Nature*; 310 (21); p. 636.

Eledjam et al.; "Effects Non Analgésiques des Morphinomimétiques"; *Cahiers d'Anesthesiologie*; 1991; 39(2); pp. 111-114.

Rosen et al., 1999, *J. Clin. Psychopharma.*, 19(1):67-85.

Schloss et al., 1998, *J. Psychopharma.*, 12(2):115-121.

Ultram® prescribing information, Physcian's Desk Reference, Medical Economics Company, 1999, 2254-57.

Effexor® (Venlafaxine HCI) achieved long-term (52 weeks) remission in 67 percent of patients with recurring depression [online] Wyeth, 2002. [retrieved on Jul. 11, 2002] Retrieved from the Internet:<URL:http://www.wyeth.com/news/Pressed_and_Released/pr05_21_2002a.asp.

Effexor XR® Venlafaxine HCI, Questions and answers about XR. atHealth.com [online] [retrieved on Jul. 11, 2002] Retrieved from the Internet:<URL:http://www.athealth.com/Consumer/mcabinet/EffexorXR.html.

Drug Information, Drug: Venlafaxine, Effexor® . Texas Cancer Online [online] [retrieved on Jul. 11, 2002] Retrieved from the Internet:<URL:http://www.jasper-web.com/texascanceronline/Drugs/effexor.htm.

Antidepressant Side Effects in Depression Patients Treated in A Naturalistic Setting: A Study of Bupropion, Moclobemide, Paroxetine, Sertraline, Venlafaxine. Canadian Psychiatric Association [online] Canadian Journal of Psychiatry [retrieved on Jul. 11, 2002]0 Retrieved from the Internet:<URL:http://www.cpa-apc.org/Publications/Archives/cjp/2002/march/orantidepressants2.asp.

Venlafaxine drug monograph. Internet Mental Health [online] [retrieved on Jul. 11, 2002] Retrieved from the Internet:<URL:http://www.mentalhealth.com/drug/p30-e02.html.

Norman, T., "The new antidepressant—mechanisms of action." [online] Experimental and Clinical Pharmacology [retrieved on Jul. 11, 2002] Retrieved from the Internet: <URL:http: www.australianprescriber.com/magazines/vol22no5/experimental1.htm.

RxList Monographs—Venlafaxine drug description. [online] [retrieved Jul. 11, 2002] Retrieved from the Internet:<URL:http://www.rxlist.com/cgi/ generic/venlafax.htm.

Goldstein, J., "Sexual aspects of headache. How sexual function relates to headaches and their causes and treatment." [online] Postgraduate Medicine [retrieved on Jul. 11, 2002] Retrieved from the Internet:<URL: http://www.postgradmed.com/issues/2001/01_01/goldstein.htm.

Ravsten, D. et al., "Spontaneous Male Orgasm in Association with Venlafaxine" *American Family Physician*, 55(5): 1561, 1564, 1574 (Apr. 1997).

Michael, A., "Venlafaxine—induced painful ejaculation," Br. J. Psychiatry, 177:282-283 (2000).

Venlafaxine (Systemic) drug description. [online] WebMD.com [retrieved on Jul. 11, 2002] Retrieved from the Internet: <URL:http://my.webmd.com/content/asset/uspdi.202764.

Effexor® Tablets drug information package enclosure. Wyeth Laboratories, revised Apr. 11, 2002.

\* cited by examiner

METHOD OF DELAYING EJACULATION

CROSS REFERENCE TO RELATED APPLICATIONS

This application claims benefit of provisional application 60/276,806, filed Mar. 16, 2001, the entire disclosure of which is considered to be part of the disclosure of this application and is hereby incorporated by reference.

FIELD OF THE INVENTION

The invention relates to a method of delaying ejaculation. In particular, the invention relates to a method of delaying ejaculation by the administration of a tramadol material.

BACKGROUND OF THE INVENTION

Premature ejaculation is a debilitating sexual dysfunction. This dysfunction can lead to an inability to enter into, or sustain, relationships and can cause psychological damage to sufferers. Premature ejaculation can also impair reproductive success.

Treatments for premature ejaculation include psychological therapies, topical anesthetics, and the use of devices. All of these treatments have significant drawbacks. Psychological therapies benefit only a subset of patients and require specialized therapists who may not be available to all patients. Furthermore, psychological therapies cannot alleviate premature ejaculation resulting from non-psychological causes. Anesthetic agents decrease sensitivity of tissues, thereby diminishing sexual pleasure. Also, topical anesthetics can be transferred to sexual partners and thereby decrease their sensitivity and pleasure as well. With regard to devices, these can be awkward, inconvenient and embarrassing to use. Devices are highly conspicuous and reveal the very condition which the suffering partner may prefer to conceal. Additionally, devices can cause irritation to one or both partners.

Methods for treating premature ejaculation by systemic administration of some antidepressant compounds (including fluoxetine, sertraline, paroxetine) have been described. See U.S. Pat. Nos. 4,507,323, 4,940,731, 5,151,448, and 5,276,042 and Rosen et al., *J. Clin. Psychopharmacol.*, 19, 67–85 (1999). However, these antidepressants may not be effective for all patients, and their side effects can halt treatment or impair patient compliance. Disease states or adverse interactions with other drugs may contraindicate the use of these compounds or require lower dosages that may not be effective to delay the onset of ejaculation.

U.S. Pat. No. 6,037,360 describes a method of treating premature ejaculation by administration of certain serotonin agonists and antagonists. A serotonin agonist is defined in this patent to be a compound which mimics the effect of serotonin on at least one of its receptors, and a serotonin antagonist is defined to be a compound which blocks the effect of serotonin on at least one of its receptors. Preferred are serotonin $5HT_3$ receptor antagonists (e.g., ondansetron, ergot alkaloids, granisetron, metoclopramide, trimethobenzamide, tropisetron, dolasetron, batanopride, and zacropride) and serotonin $5HT_4$ agonists (e.g., cisapride and D-lysergic acid diethylamide). Unfortunately, these compounds have side effects which may contraindicate their use (e.g., ergot alkaloids and D-lysergic acid diethylamide) or have limited effectiveness (e.g., metoclopramide and the like; see PCT application WO 95/13072).

Thus, a need clearly exists for other methods of treating premature ejaculation. In particular, there is a need for a method of treating premature ejaculation that requires no specialized psychological therapy, can be used conveniently and without embarrassment, and does not involve the problems associated with prior therapeutic methods.

Tramadol is a centrally acting synthetic analgesic compound. Its mode of action is not completely understood. From animal tests, at least two complementary mechanisms appear applicable: (1) the binding of the parent compound (tramadol) and the O-demethylated M1 metabolite to $\mu$-opioid receptors; and (2) a weak inhibition of reuptake of norepinephrine and serotonin. Opioid activity is due to both low affinity binding of the parent compound and higher affinity binding of the M1 metabolite to $\mu$-opioid receptors. In animal models, M1 is up to 6 times more potent than tramadol in producing analgesia and 200 times more potent in $\mu$-opioid binding. Tramadol has been shown to inhibit reuptake of norepinephrine and serotonin in vitro, as have some other opioid analgesics. These mechanisms may contribute independently to the overall analgesic profile of tramadol.

Apart from analgesia, the use of tramadol to treat frequent urination and urinary incontinence (see U.S. Pat. No. 6,090,856) and to treat coughs, bronchitis and the common cold (see U.S. Pat. Nos. 3,652,589 and 3,830,934) have been described. There is no teaching or suggestion in the prior art that tramadol could be used to delay ejaculation.

SUMMARY OF THE INVENTION

The invention provides a method of delaying ejaculation. The method comprises administering an effective amount of a tramadol material to a human male prior to sexual intercourse.

DETAILED DESCRIPTION OF THE PRESENTLY-PREFERRED EMBODIMENTS OF THE INVENTION

The term "premature ejaculation" as used herein means a sexual dysfunction wherein a male is unable to control the ejaculatory process to a degree sufficient to satisfy a partner. Generally, premature ejaculation refers to persistent or recurring ejaculation with minimal stimulation before or during sexual intercourse. The term includes both "congenital" or "lifelong" premature ejaculation and "primary" or "acquired" premature ejaculation. Specific definitions include: (i) ejaculation prior to penetration or within ten to twenty strokes after intromission; (ii) ejaculation in less than 1–2 minutes; and (iii) ejaculation 50% of the time more rapidly than the female is able to have an orgasm if she has no orgasmic dysfunction. See, e.g., U.S. Pat. No. 6,037,360 and 5,151,448; *Male Infertility and Sexual Dysfunction,* page 356 (Springer-Verlag 1997); *Diagnostic and Statistical Manual of Mental Disorders* (American Psychiatric Association 1994). Premature ejaculation, however defined, can be treated by the method of the invention.

As used herein, "delay ejaculation" means that a male receiving a tramadol material is able to control the ejaculatory process so as to prevent ejaculation for a time which is longer than that normally experienced by the male when not receiving the tramadol material. It is expected that, in the case of a male who suffers from premature ejaculation, the male will be able to control the ejaculatory process to a degree sufficient to better or completely satisfy his partner. "Delay ejaculation" does not mean to totally prevent ejaculation.

The term "tramadol material" is used herein to refer to 2-[(dimethylamino)methyl]-1-(3-methoxyphenyl)-cyclohexanol ("tramadol") and all pharmaceutically-acceptable forms and derivatives of tramadol. In particular, the term includes the N-oxide derivative ("tramadol N-oxide") and the O-desmethyl derivative ("O-desmethyl tramadol"). The term also includes the solvates, polymorphs, and pharmaceutically-acceptable acid addition salts of tramadol and its derivatives. The term further includes all of the stereoisomers of any of the foregoing, including individual stereoisomers (including individual enantiomers) and mixtures of stereoisomers (including the racemates).

Figure 1:
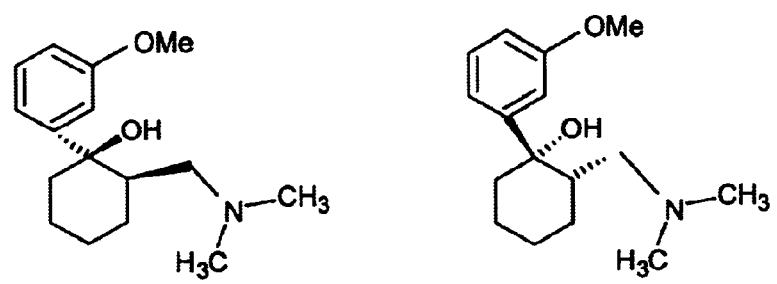
FIG. 1 shows stereoisomers of tramadol.
Figure 1:
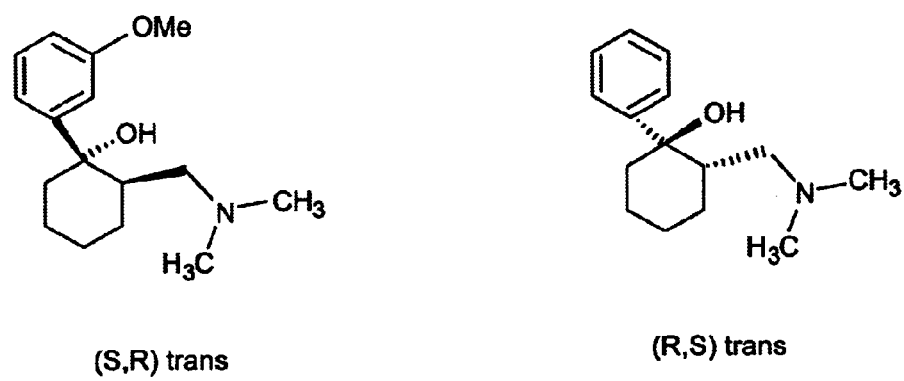

The stereoisomers of tramadol are shown in FIG. 1. There appears to be some discrepancy in the literature regarding the nomenclature of the individual stereoisomers of tramadol. For the purposes of the present application, the designations of "cis" and "trans" stereoisomers of tramadol are made in reference to the relative positions of the dimethylamino and the hydroxy substituents on the cyclohexane ring within the tramadol molecule. As shown in FIG. 1, the R,R and S,S enantiomers will be referred to herein as the "cis" isomers while the R,S and S,R isomers will be referred to herein as the "trans" isomers. As also shown in FIG. 1, the R,R isomer of tramadol will be referred to herein as the "+" cis isomer and the S,S isomer will be referred to as the "−" cis isomer. It is presently understood that R,S and S,R isomers are not optically active.

Presently preferred is tramadol and the acid addition salts thereof, particularly the hydrochloride. Even more preferred is (±)cis-tramadol, the acid addition salts, particularly the hydrochloride, and the individual enantiomers.

Methods of making tramadol, tramadol N-oxide, and O-desmethyl tramadol are well known. See, e.g. U.S. Pat. Nos. 3,652,589, 3,830,934, 5,223,541, 5,336,691, 5,723,668, 5,728,885, and 5,874,620, the complete disclosures of which are incorporated herein by reference. Tramadol is also commercially available from Gruenenthal GmbH, Aschen, Germany.

The pharmaceutically-acceptable acid addition salts are prepared by conventional methods well known in the art using pharmaceutically-acceptable, substantially non-toxic, organic and inorganic acids. Such acids include hydrochloric acid, nitric acid, sulfuric acid, phosphoric acid, hydrobromic acid, acetic acid, propionic acid, maleic acid, malonic acid, succinic acid, citric acid, tartaric acid, malic acid, benzoic acid, salicylic acid, phthalic acid, nicotinic acid, etc. Preferred is hydrochloric acid, and tramadol hydrochloride is the most preferred compound for practicing the invention.

To delay ejaculation, an effective amount of a tramadol material is administered to a male prior to sexual intercourse. By an "effective amount" is meant a nontoxic, but sufficient, amount of a tramadol material to delay ejaculation. Effective dosage forms, modes and times of administration, and dosage amounts maybe determined empirically, and making such determinations is within the skill of the art. Preferred is a single dose taken orally shortly before sexual intercourse. In particular, it has been found that an effective dosage of (±)cis-2-[(dimethylamino)methyl]-1-(3-methoxyphenyl)-cyclohexanol hydrochloride to delay ejaculation is from about 10 to about 50 milligrams (mg), preferably from about 15 to about 35 mg, most preferably about 25 mg, administered orally from about 30 to about 60 minutes prior to sexual intercourse. However, it is understood by those skilled in the art that the dosage amount will vary with the particular form of tramadol employed, the route(s) of administration, the timing of the administration, the identity of any other drugs being administered, whether or not the male suffers from premature ejaculation and the severity of the premature ejaculation condition, the age, size and condition of the patient, and like factors known in the medical art. In general, a suitable dose will be that amount of the compound which is the lowest dose effective to delay ejaculation without toxicity. However, the dosage, route of administration, etc., will be determined by an attending physician within the scope of sound medical judgement.

The tramadol material may be administered by any suitable route of administration, including orally, nasally, rectally, parenterally (e.g., intravenously, subcutaneously, or intramuscularly), topically (i.e., delivery to the skin or mucosa), transdermally (i.e., delivery by passage of a drug through the skin into the bloodstream), transmucosally (i.e., delivery by passage of a drug through the mucosal tissue into the bloodstream), intracavernosally (i.e., injection into one or both corpora of the corpora cavernosal tissues of the penis), and intarurethrally (i.e., delivery into the urethra). Highly preferred is oral administration.

While it is possible for the tramadol material to be administered alone, it is preferable to administer it as a pharmaceutical formulation (composition). The pharmaceutical compositions will comprise a tramadol material as the active ingredient in admixture with one or more pharmaceutically-acceptable carriers and, optionally, with one or more other compounds, drugs, or other materials. Each carrier must be "acceptable" in the sense of being compatible with the other ingredients of the formulation and not injurious to the male who will take the composition. Pharmaceutically-acceptable carriers are well known in the art. Regardless of the route of administration selected, the active ingredients are formulated into pharmaceutically-acceptable dosage forms by conventional methods known to those of skill in the art. See, e.g., *Remington's Pharmaceutical Sciences*.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of the active ingredient. Preferred oral administration forms are tablets and capsules.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monosterate; (8) absorbents, such as kaolin and bentonite clay; (9) lubricants, such as talc, calcium stearate, magnesium stearate, solid polyethylene glycols, sodium lauryl sulfate, and mixtures thereof, and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

A tablet may be made by compression or molding optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient only, or preferentially, in a certain portion of the gastrointestinal tract, optionally, in a delayed manner. Examples of embedding compositions which can be used include polymeric substances and waxes. The active ingredient can also be in microencapsulated form.

Liquid dosage forms for oral administration of the compounds of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming, thickening, and preservative agents.

Suspensions, in addition to the active ingredient, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal administration may be presented as a suppository, which may be prepared by mixing one or more compounds of the invention with one or more suitable nonirritating excipients or carriers comprising, for example, cocoa butter, polyethylene glycol, a suppository wax or salicylate, and which is solid at room temperature, but liquid at body temperature and, therefore, will melt in the rectum and release the active ingredient.

Dosage forms for the topical, transdermal or transmucosal administration of the active ingredient include powders, sprays, ointments, pastes, creams, lotions, gels, solutions, patches, drops and inhalants. The active ingredient may be mixed under sterile conditions with a pharmaceutically-acceptable carrier, and with any buffers, or propellants which may be required.

The ointments, pastes, creams and gels may contain, in addition to the active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the active ingredient, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane.

The active ingredient may also be delivered through the skin using conventional transdermal drug delivery systems, i.e., transdermal patches, wherein the agent is typically contained within a laminated structure that serves as a drug delivery device to be affixed to the skin. In such a structure, the active ingredient is typically contained in a layer, or "reservoir," underlying an upper backing layer. The laminated device may contain a single reservoir, or it may contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form.

The backing layer in these laminates, which serves as the upper surface of the device, functions as the primary structural element of the laminated structure and provides the device with much of its flexibility. The material selected for the backing material should be selected so that it is substantially impermeable to the active ingredient and any other materials that are present. The backing layer may be either occlusive or nonocclusive, depending on whether it is desired that the skin become hydrated during drug delivery. The backing is preferably made of a sheet or film of a preferably flexible elastomeric material. Examples of polymers that are suitable for the backing layer include polyethylene, polypropylene, polyesters, and the like.

During storage and prior to use, the laminated structure includes a release liner. Immediately prior to use, this layer is removed from the device to expose the basal surface thereof, either the drug reservoir or a separate contact adhesive layer, so that the system may be affixed to the skin. The release liner should be made from a drug/vehicle impermeable material.

Transdermal drug delivery devices maybe fabricated using conventional techniques, known in the art, for example by casting a fluid admixture of adhesive, drug and vehicle onto the backing layer, followed by lamination of the release liner. Similarly, the adhesive mixture may be cast onto the release liner, followed by lamination of the backing layer. Alternatively, the drug reservoir may be prepared in the absence of drug or excipient, and then loaded by "soaking" in a drug/vehicle mixture.

The laminated transdermal drug delivery systems may in addition contain a skin permeation enhancer. That is, because the inherent permeability of the skin to some drugs may be too low to allow therapeutic levels of the drug to pass through a reasonably sized area of unbroken skin, it is necessary to coadminister a skin permeation enhancer with such drugs. Suitable enhancers are well known in the art.

The pharmaceutical compositions of the invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, propellants such as fluorocarbons or nitrogen, and/or other conventional solubilizing or dispersing agents.

Preferred formulations for topical drug delivery are ointments and creams. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Formulations for buccal administration include tablets, lozenges, gels and the like. Alternatively, buccal administration can be effected using a transmucosal delivery system as known to those skilled in the art.

Pharmaceutical compositions suitable for parenteral administrations comprise the active ingredient in combination with one or more pharmaceutically-acceptable sterile isotonic aqueous or non-aqueous solutions, dispersions, suspensions or emulsions, or sterile powders or other solid forms which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of injectable pharmaceutical forms may be brought about by the inclusion of agents which delay absorption such as aluminum monosterate and gelatin.

In some cases, in order to prolong the effect of the active ingredient, it is desirable to slow the absorption of the active ingredient from subcutaneous or intramuscular injection. This may be accomplished by the use of a liquid suspension of crystalline or amorphous material having poor water solubility. The rate of absorption of the active ingredient then depends upon its rate of dissolution which, in turn, may depend upon crystal size and crystalline form. Alternatively, delayed absorption of a parenterally-administered active ingredient is accomplished by dissolving or suspending the drug in an oil vehicle.

Injectable depot forms are made by forming microencapsule matrices of the active ingredient in biodegradable polymers such as polylactide-polyglycolide. Depending on the ratio of active ingredient to polymer, and the nature of the particular polymer employed, the rate of release of the active ingredient can be controlled. Examples of other biodegradable polymers include poly(orthoesters) and poly (anhydrides). Depot injectable formulations are also prepared by entrapping the active ingredient in liposomes or microemulsions which are compatible with body tissue. The injectable materials can be sterilized for example, by filtration through a bacterial-retaining filter.

Intracavernosal injection can be carried out by use of a syringe or any other suitable device. An example of a hypodermic syringe useful herein, that can be used for simultaneous injection into both corpora, is described in U.S. Pat. No. 4,127,118. The injection is made on the dorsum of the penis by placement of the needle to the side of each dorsal vein and inserting it deep into the corpora.

The active ingredient can be administered in a pharmaceutical formulation suitable for transurethral drug delivery. The formulation contains one or more selected carriers or excipients, such as water, silicone, waxes, petroleum jelly, polyethylene glycol, propylene glycol, liposomes, sugars such as mannitol and lactose, and/or a variety of other materials, with polyethylene glycol and derivatives thereof particularly preferred. It may be desirable to incorporate a transurethral permeation enhancer in the urethral dosage form. Examples of suitable transurethral permeation enhancers include dimethylsulfoxide, dimethyl formaminde, N,N-dimethylacetamide, decylmethylsulfoxide, polyethylene glycol monolaurate, glycerol monolaurate, lecithin, the 1-substituted azacycloheptan-2-ones, particularly 1-n-dodecylcyclazacycloheptan-2-one (available under the trademark Azone® from Nelson Research & Development Co., Irvine, Calif.), SEPA® (available from Macrochem Co., Lexington, Mass.), alcohols (e.g., ethanol), detergents (such as Tergitol®, Nonoxynol-9® and TWEEN-80®) and the like. Transurethral formulations may additionally include one or more enzyme inhibitors effective to inhibit drug-degrading enzymes which may be present in the urethra. Additional optional components include excipients, preservatives (e.g., antioxidants), chelating agents, solubilizing agents (e.g., surfactants), and the like, as will be appreciated by those skilled in the art of drug formulation preparation and delivery.

Transurethral drug administration, as explained in PCT application WO 91/16021, can be carried out in a number of different ways using a variety of urethral dosage forms. For example, the drug can be introduced into the urethra from a flexible tube, squeeze bottle, pump or aerosol spray. The drug may also be contained in coatings, pellets or suppositories which are absorbed, melted or bioeroded in the urethra. In certain embodiments, the drug is included in a coating on the exterior surface of a penile insert. Drug delivery devices for administering a drug transurethrally are described in U.S. Pat. No. 6,037,360 and PCT application WO 91/16021.

Urethral suppository formulations containing polyethylene glycol or a polyethylene glycol derivative can be used as the urethral dosage form, and may be conveniently formulated using conventional techniques, e.g., compression molding, heat molding or the like, as will be appreciated by those skilled in the art and as described in the pertinent literature and pharmaceutical texts. See, for example, *Remington: The Science and Practice of Pharmacy,* 19th Ed. (Easton, Pa.: Mack Publishing Co., 1995), which discloses typical methods of preparing pharmaceutical compositions in the form of urethral suppositories. It is also preferred that urethral suppositories contain one or more solubilizing agents (e.g., a nonionic, anionic, cationic or amphoteric surfactant) effective to increase the solubility of the active ingredient in the polyethylene glycol or other transurethral vehicle.

It may be desirable to deliver the active ingredient in a urethral dosage form which provides for controlled or sustained release of the agent. In such a case, the dosage form typically comprises a biocompatible, biodegradable material, typically a biodegradable polymer. Examples of such polymers include polyester, polyalkylcyanoacrylate, polyorthoester, polyanhydride, albumin, gelatin and starch. As explained, for example, in PCT application WO 96/40054, these and other polymers can be used to provide biodegradable microparticles which enable controlled and sustained drug release, in turn minimizing the required dosing frequency.

The method of intraurethral administration may involve an "active" delivery mechanism such as iontophoresis, electroporation or phonophoresis. Devices and methods for delivering drugs in this way are well known in the art. Iontophoretically assisted drug delivery is, for example, described in PCT application WO 96/40054. Briefly, the active agent is driven through the urethral wall by means of an electric current passed from an external electrode to a second electrode contained within or affixed to a urethral probe.

The pharmaceutical formulations of the tramadol material may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions maybe prepared from sterile powders, granules and tablets of the type described above.

Pharmaceutical compositions containing a tramadol material and methods of making the pharmaceutical compositions have been described. See, e.g., U.S. Pat. Nos. 3,652,589, 3,830,934, 5,223,541, 5,591,452, 5,601,842, 5,728,885, 6,017,963, 6,090,856, and 6,156,342, the complete disclosures of which are incorporated herein by reference. Moreover, pharmaceutical compositions containing tramadol and pharmaceutically-acceptable salts thereof are manufactured and sold worldwide. In the United States, (±)cis-2-[(dimethylamino)methyl]-1-(3-methoxyphenyl)-cyclohexanol hydrochloride for oral administration is available from Ortho-McNeil Pharmaceutical, Inc., Raritan, N.J. 08869, as ULTRAM tablets. Each ULTRAM tablet contains 50 mg (±)cis-2-[ (dimethylamino)methyl]-1-(3-methoxyphenyl)-cyclohexanol hydrochloride and a number of inactive ingredients (corn starch, hydroxypropyl methylcellulose, lactose, magnesium stearate, microcrystalline cellulose, polyethylene glycol, polysorbate 80, sodium starch glycolate, titanium dioxide and wax). It is understood the commercial preparation of tramadol marketed under the brand name ULTRAM® consists of a mixture of the R,R and S,S isomers of tramadol hydrochloride.

EXAMPLES

Example 1

Tramadol Hydrochloride Delays Ejaculation

A tramadol material at doses of 10 mg and higher, taken approximately 30–60 minutes prior to sexual intercourse by the male partner delays ejaculation significantly. It was observed, for example, that a dose of 25 mg tramadol hydrochloride (one-half of a 50 mg ULTRAM tablet, Ortho-McNeil Pharmaceutical, Inc., Raritan, N.J.) taken orally 30–60 minutes prior to sexual intercourse delayed ejaculation by a normal male subject by at least 10–15 minutes. At doses of 50–100 mg, a similar effect was observed. However, it was associated with drowsiness, lightheadedness, dry mouth and a sense of slight euphoria (opioid effect) and, at 100 mg, sometimes ejaculation/orgasm was not achieved. From these observations, it was concluded that a dose of 10–50 mg of a tramadol material, preferably 15–35 mg, most preferably 25 mg, can delay ejaculation significantly and can be used to treat (prevent or reduce) premature ejaculation.

I claim:

1. A method of delaying ejaculation during sexual intercourse comprising administering orally to a human male who suffers from premature ejaculation prior to the sexual intercourse an effective amount of a compound selected from the group consisting of tramadol, a pharmaceutically-acceptable form of tramadol, tramadol-oxide, a pharmaceutically-acceptable form of tramadol N-oxide, O-desmethyl tramadol, a pharmaceutically-acceptable form of O-desmethyl tramadol and mixtures of the foregoing.

2. The method of claim 1 wherein the compound is tramadol or a pharmaceutically-acceptable salt thereof.

3. The method of claim 2 wherein the tramadol is (±) cis-tramadol or a pharmaceutically-acceptable salt thereof.

4. The method of claim 3 wherein a dose of from about 10 to about 50 milligrams of the tramadol or the pharmaceutically-acceptable salt thereof is administered to the male.

5. The method of claim 4 wherein a dose of from about 15 to about 35 milligrams of the tramadol or the pharmaceutically-acceptable salt thereof is administered to the male.

6. The method of claim 4 wherein a dose of about 25 milligrams of the tramadol or the pharmaceutically-acceptable salt thereof is administered to the male.

7. The method of claim 3 wherein a (+)-enantiomer of the cis-tramadol or the pharmaceutically-acceptable salt thereof is administered to the male.

8. The method of claim 3 wherein a (−)-enantiomer of the cis-tramadol or the pharmaceutically-acceptable salt thereof is administered to the male.

9. The method of claim 3 wherein the tramadol material is (±) cis-tramadol hydrochloride.

10. The method of claim 9 wherein a dose of from about 10 to about 50 milligrams of the tramadol hydrochloride is administered to the male.

11. The method of claim 10 wherein a dose of from about 15 to about 35 milligrams of the tramadol hydrochloride is administered to the male.

12. The method of claim 10 wherein a dose of about 25 milligrams of the tramadol hydrochloride is administered to the male.

13. The method of any one of claims 1–12 or 14–17 wherein the compound is administered from about 30 minutes to about 60 minutes prior to sexual intercourse.

14. The method of claim 4 wherein a dose of from about 10 to about 35 milligrams of the tramadol or the pharmaceutically-acceptable salt thereof is administered to the male.

15. The method of claim 4 wherein a dose of from about 25 to about 35 milligrams of the tramadol or the pharmaceutically-acceptable salt thereof is administered to the male.

16. The method of claim 10 wherein a dose of from about 10 to about 35 milligrams of the tramadol or the pharmaceutically-acceptable salt thereof is administered to the male.

17. The method of claim 10 wherein a dose of from about 25 to about 35 milligrams of the tramadol or the pharmaceutically-acceptable salt thereof is administered to the male.

* * * * *